United States Patent [19]

Ikeda et al.

[11] Patent Number: 5,521,212
[45] Date of Patent: May 28, 1996

[54] CYCLOPROPYL N-HYDROXYUREA AND N-HYDROXYACETAMIDES WHICH INHIBIT LIPOXYGENASE

[75] Inventors: Takafumi Ikeda; Akiyoshi Kawai; Takashi Mano, all of Handa; Yoshiyuki Okumura, Aichi; Rodney W. Stevens, Handa, all of Japan

[73] Assignee: Pfizer Inc., New York, N.Y.

[21] Appl. No.: 244,739

[22] PCT Filed: Oct. 27, 1992

[86] PCT No.: PCT/US92/08979

§ 371 Date: Aug. 26, 1991

§ 102(e) Date: Aug. 26, 1991

[30] Foreign Application Priority Data

Dec. 13, 1991 [JP] Japan ................ 3-330485

[51] Int. Cl.$^6$ .................. A61K 31/40; A61K 31/33; A61K 31/445; C07D 295/195
[52] U.S. Cl. .................. 514/428; 514/183; 514/210; 514/331; 514/575; 546/234; 548/568; 548/950; 548/967; 562/621; 562/623
[58] Field of Search .................. 562/623, 621; 548/568; 514/575, 428

[56] References Cited

U.S. PATENT DOCUMENTS

| 4,822,809 | 4/1989 | Summers et al. | 514/367 |
| 5,037,853 | 8/1991 | Brooks et al. | 514/595 |
| 5,120,752 | 6/1992 | Brooks et al. | 514/346 |

FOREIGN PATENT DOCUMENTS

| 0436199 | 7/1991 | European Pat. Off. |
| 0452908 | 10/1991 | European Pat. Off. |
| W090/08545 | 8/1990 | WIPO |

OTHER PUBLICATIONS

J. March, Advanced Organic Chemistry, J. Wiley, & Sons, 1992, p. 412.
Aldrich Catalogue, Aldrich Chemical Co. (Milwaukee, WI), 1994, pp. 120, 1148.

*Primary Examiner*—Joseph Paul Brust
*Attorney, Agent, or Firm*—Peter C. Richardson; Paul H. Ginsburg; Bryan C. Zielinski

[57] ABSTRACT

Compounds of the formula

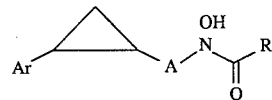

wherein A is C1 to C3 alkylene, Ar is phenyl or styryl, R is halosubstituted C1 to C3 alkyl, NHR' or

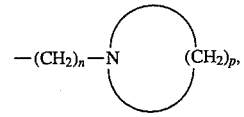

R' is hydrogen or C2 to C8 alkylthioalkyl, n is an integer of from 1 to 4 and p is an integer of from 2 to 5, with the proviso that when R' is hydrogen then Ar is styryl, and the pharmaceutically acceptable salts thereof, inhibit the enzyme lipoxygenase and are useful in treating allergy and inflammatory and cardiovascular conditions for which the action of lipoxygenase has been implicated. These compounds form the active ingredient in pharmaceutical compositions for treating such conditions.

11 Claims, No Drawings

CYCLOPROPYL N-HYDROXYUREA AND N-HYDROXYACETAMIDES WHICH INHIBIT LIPOXYGENASE

This application is a 371 of PCT US92/08979 filed Oct. 27, 1992.

BACKGROUND OF THE INVENTION

FIELD OF THE INVENTION

This invention relates to novel cyclopropyl N-hydroxyurea end N-hydroxyacetamide derivatives. The compounds of the present invention inhibit the action of the enzyme lipoxygenase end are useful in the treatment or alleviation of inflammatory diseases, allergy end cardiovascular diseases in mammals. This invention also relates to pharmaceutical compositions comprising such compounds end to the use of such compounds in treating inflammatory diseases, allergy end cardiovascular diseases in mammals. This invention further relates to methods of making such compounds.

Arachidonic acid is known to be the biological precursor of several groups of endogenous metabolites, prostaglendins including prostacydins, thromboxenes end leukotrienes. The first step of arachidonic acid metabolism is the release of arachidonic acid end related unsaturated fatty acids from membrane phospholipids, via the action of phospholipase. Free fatty acids are then metabolized either by cyclooxygenase to produce the prostaglendins end thromboxenes or by lipoxygenase to generate hydroperoxy fatty acids which may be further converted to the leukotrienes. Leukotrienes have been implicated in the patiophysiology of inflammatory diseases, including rheumatoid arthritis, gout, asthma, ischemia reperfusion injury, psoriasis end inflammatory bowel disease. Any drug that inhibits lipoxygenase is expected to provide significant new therapy for both acute end chronic inflammatory conditions.

Several review articles on lipoxygenase inhibitors have been reported (See H. Masamune et ed., *Ann. Rep. Med. Chem.*, 24, 71–80 (1989) end B. J. Fitzsimmons et al., *Leukotrienes and Lipoxygenases*, 427–502 (1989).

Compounds of the same general class as the compounds of the present invention are disclosed in EP 279263 A2, EP 196184 A2, EP 436199 A, JP (Kohyo) 502179/88, JP (Appln.) 105648/90 and U.S. Pat. No. 4,822,809.

SUMMARY OF THE INVENTION

The present invention provides novel cyclopropyl N-hydroxyurea and N-hydroxyacetamide derivatives of the following formula and their pharmaceutically acceptable salts.

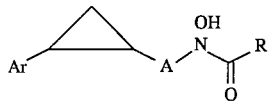

wherein A is C1 to C3 alkylene, Ar is phenyl or styryl, R is halosubstituted C1 to C3 alkyl, NHR' or

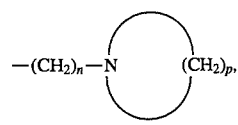

R' is hydrogen or C2 to C8 alkytthioalkyl, n is an integer of from 1 to 4 and p is an integer of from 2 to 5, with the proviso that when R' is hydrogen then Ar is styryl.

This invention also concerns pharmaceutical compositions comprising a pharmaceutically acceptable carrier or diluent and a compound of the invention or a pharmaceutically acceptable salt thereof. This invention further concerns methods of treating inflammatory diseases, allergy and cardiovascular diseases in mammals comprising administration of such compounds or compositions.

DETAILED DESCRIPTION OF THE INVENTION

Definitions

As used herein, the following definitions are used.

"Halo" and "halogen" mean radicals derived from the elements fluorine, chlorine, bromine and iodine.

"Alkyl" means straight or branched saturated hydrocarbon radicals, for example, methyl, ethyl, n-propyl and isopropyl.

"Halosubstituted alkyl" refers to an alkyl radical as described above substituted with one or more halogen radicals, for example, chloromethyl, bromoethyl and trifluoromethyl.

"Alkylene" means straight or branched alkene radicals, for example, methylene, 1,2-ethylene, 1,3-propylene and 1,2-propylene.

"Alkylthioalkyl" means a group of the structure -RSR wherein R is alkyl as defined above, for example, methylthiomethyl, methylthioethyl, methylthiopropyl, ethylthioethyl and propylthiomethyl.

This invention includes pharmaceutical compositions for treatment of inflammatory diseases, allergy and cardiovascular diseases in a mammal which comprises a pharmaceutically acceptable carrier or diluent and a compound of the above formula or a pharmaceutically acceptable salt thereof.

This invention also includes pharmaceutical compositions for inhibiting the lipoxygenase in mammal which comprises a pharmaceutically acceptable carrier and a compound of the above formula or a pharmaceutically acceptable salt thereof.

The novel compounds of this invention may be prepared as shown in the reaction scheme described below.

GENERAL SYNTHETIC SCHEME

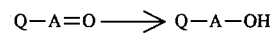

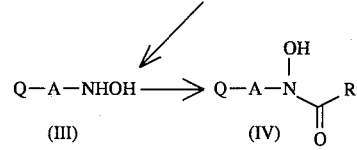

In the above scheme, A and R are as previously defined and Q is

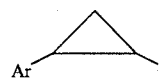

wherein Ar is phenyl or styryl.

The compounds of the invention are prepared according to the reaction steps explained in detail as follows.

The starting materials used in the procedure of the above reaction scheme may be prepared from commercially available compounds or known compounds according to standard methods known in the art.

In the first step, an alcohol (II) can be prepared via reduction of the corresponding ketone (I) with suitable reducing agent(s). Subsequently, the corresponding hydroxylamine (III) can be prepared by treating said alcohol with N,O-bis(tert-butoxycarbonyl)hydroxylamine under Mitsunobu-type reaction conditions followed by acid-catalyzed hydrolysis of the N,O-protected intermediate product (sea JP (Kokai) 45344/89).

For example, ketone (I) is treated with tetrahydrofuran (THF) and a reducing agent (LiAlH$_4$, LiAlH(OC(CH$_3$)$_3$)$_3$ and the like) in a reaction-inert solvent. Preferred solvents include benzene, toluene, Et$_2$O, THF and methylene chloride. The reaction is usually carded out in the temperature range of from about −80° to about reflux temperature, with reaction times generally from several minutes to about 24 hours. The hydroxylamine thus obtained can be isolated by standard methods and purification can be achieved by conventional means, such as by recrystallization end chromatography.

The acetamides (IV) of the present invention can be prepared by treating the hydroxylamine with substituted acetyl chloride. For example, the hydroxylamine is reacted with acetyl chloride or the like in a reaction-inert solvent in the presence of a suitable base. Preferred bases include trimethylamine and pyridine; sodium hydride can also be used. Suitable solvents include methylene chloride, chloroform, THF, benzene end toluene. The reaction is usually carried out in the temperature range of from about 0° C. to about room temperature, with reaction times generally from about 30 minutes to several hours. The final product acetamide (IV) can be isolated and purified by conventional means, such as by recrystallization and chromatography.

The ureas (IV) of the present invention can be prepared by treating the hydroxylamine (III) with a suitable isocyanate corresponding to the desired final product in a reaction-inert solvent. The reaction is usually carried out in the range of from room temperature through to reflux temperature. Suitable solvents which do not react with the hydroxylamine and/or isocyanate include, for example, THF, dioxane, methylene chloride and benzene. Preferred isocyanates include chloropropyl isocyanate, isocyanate propionic acid and trimethylsilyl isocyanate. The final product urea (IV) can be isolated and purified by conventional means, such as by recrystallization and chromatography.

The pharmaceutically acceptable salts of the novel compounds of the present invention are readily prepared by contacting said compounds with a stoichiometric amount of, in the case of a non-toxic cation, an appropriate metal hydroxide or alkoxide or amine in either aqueous solution or a suitable organic solvent, or, in the case of a non-toxic acid salt, an appropriate mineral or organic acid in either aqueous solution or a suitable organic solvent. The salt may then be obtained by precipitation or by evaporation of the solvent.

While the compounds of the present invention produced by the methods outlined above are racemic mixtures, they can be resolved into optically active isomers via known processes.

The compounds of this invention inhibit the activity of the enzyme lipoxygenase. This inhibition has been demonstrated by an assay using rat peritoneal cavity-resident calls which determines the effect of said compounds on the metabolism of arachidonic acid.

All of the compounds of Examples 1 to 4 were tested according to the methods described in "Synthesis of leukotrienes by peritoneal macrophages," *Jap. J. Inflammation*, 7, 145–150 (1987), and were shown to be lipoxygenase inhibitors, exhibiting IC$_{50}$ values in the range of about 0.186 to about 24.5 µM, for lipoxygenase inhibition.

The ability of the compounds of the present invention to inhibit lipoxygenase makes them useful for controlling the symptoms induced by the endogenous metabolites arising from arachidonic acid in a mammalian subject. The compounds are therefore valuable in the prevention and treatment of such disease states in which the accumulation of arachidonic acid metabolites are the causative factor, e.g., allergic bronchial asthma, skin disorders, rheumatoid arthritis, osteoarteritis and thrombosis.

The compounds of the invention and their pharmaceutically acceptable salts are of particular use in the treatment or alleviation of inflammatory diseases, allergy and cardiovascular diseases in a human subject as well in the inhibition of lipoxygenase.

Methods of Administration

For treatment of the various conditions described above, the compounds of the invention and their pharmaceutically acceptable salts can be administered to a human subject either alone or, preferably, in combination with pharmaceutically acceptable carriers or diluents in a pharmaceutical composition, according to standard pharmaceutical practice. A compound can be administered via a variety of conventional routes of administration including orally, parenterally and by inhalation. When the compounds are administered orally, the dose range will generally be from about 0.1 to about 20 mg/kg/day, based on the body weight of the subject to be treated, preferably from about 0.1 to about 1.0 mg/kg/day in single or divided doses. If parenteral administration is desired, then an effective dose will generally be from about 0.1 to about 1.0 mg/kg/day. In some instances it may be necessary to use dosages outside these limits, since the dosage will necessarily vary according to the age, weight and response of the individual patient as well as the severity of the patient's symptoms and the potency of the particular compound being administered.

For oral administration, the compounds of the invention and their pharmaceutically acceptable salts can be administered, for example, in the form of tablets, powders, lozenges, syrups or capsules, or as an aqueous solution or suspension. In the case of tablets for oral use, carriers which are commonly used include lactose and corn starch. Lubricating agents such as magnesium stearate are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added.

For intramuscular, intraperitoneal, subcutaneous and intravenous use, a sterile solution of the active ingredient is usually prepared, and the pH of the solutions should be suitably adjusted and buffered. For intravenous use, the total concentration of solute should be controlled to make the preparation isotonic.

EXAMPLES

The present invention is illustrated by the following examples. However, it should be understood that the invention is not limited to the specific details of these examples.

Proton nuclear magnetic resonance spectra (NMR) were measured at 270 MHz unless otherwise indicated and peak positions are expressed in parts per million (ppm) downfield from tetramethylsilane. The peak shapes are denoted as follows: s, singlet; d, doublet; t, triplet; q, quartet; m, multiplet; br, broad.

EXAMPLE 1
N-hydroxy-N-[(2-trans-styrylcyclopropyl)methyl]urea

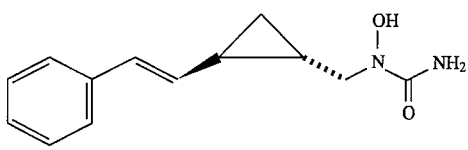

To a stirred solution of N,O-bis(t-butoxycarbonyl)-N-[(2-trans-styryl-1-cyclopropyl)methyl]hydroxylamine (3.7 g, 9.5 mM) in methylene chloride (30 ml) was added trifluoroacetic acid (5.42 g) dropwise at 5° C. After stirring for 1.5 hours, the volatiles were removed in vacuo. Saturated aqueous sodium bicarbonate (50 ml) was added, and the whole extracted with ethyl acetate (2×100 ml, 50 ml). The organic layer was washed with water (100 ml) and brine (100 ml), then was added over magnesium sulfate and evaporated in vacuo to afford 1.94 g (78.7% yield) of the corresponding hydroxylamine.

To a stirred solution of said hydroxylamine (1.94 g, 10.26 mM) in dry THF (20 ml) was added trimethylsilyl isocyanate (1.71 g, 13.34 mM) at room temperature under a nitrogen atmosphere. After stirring overnight, methanol (20 ml) was added to quench the reaction, volatiles were removed in vacuo, and the resulting solid was recrystallized from ethyl acetate/n-hexane, providing 0.84 g (38% yield) of the desired product as colorless crystals, m.p. 138°–139° C. (dec.).

IR (nujol): 3460, 1615, 1575, 1155, 990, 950, 740, 690.

NMR (CDCl$_3$): 9.05 (s, 1H), 7.32 (s, 5H), 6.44 (d, J=15.4 Hz, 1H), 5.78 (dd, J=8.8, 15.4 Hz, 1H), 5.38 (br s, 2H), 3.54 (dd, J=6.6, 15 Hz, 1H), 3.43 (dd, J=7.4, 15 Hz, 1H), 1.58 (m, 1H), 1.35 (m, 1H), 0.81 (m, 2H).

EXAMPLE 2
N-hydroxy-N'-(3-methylthiopropyl)-N-[(trans-2-phenylcyclopropyl)methyl]urea

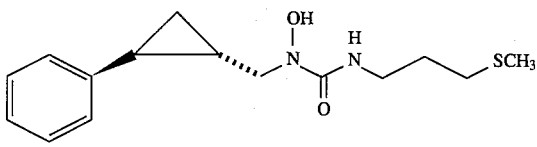

To a stirred solution of N'-(3-chloropropyl)-N-hydroxy-N-[(trans-2-phenyleyclopropyl)methyl]urea (0.79 g, 2.8 mM) in dry THF (10 ml) was added sodium thiomethoxide (0.5 g, 16.7 mM) at room temperature. After stirring overnight, it was poured into saturated aqueous ammonium chloride. The whole was extracted with ethyl acetate (2×120 ml). The extracts were washed with water and brine, then were dried and evaporated in vacuo. The product was recrystallized from ethyl acetate/n-hexane, vacuum filtered and dried to furnish 0.82 g (35% yield) of the desired product, m.p. 103°–104° C.

IR (neat): 3.360, 1590, 1550, 1255, 1160, 1110, 750, 690.

NMR (DMSO-d6): 9.23 (s, 1H), 7.14 (m, 5H), 6.97 (t, J=6.2 Hz, 1H), 3.35 (m, 2H), 3.11 (q, J=6.6 Hz, 2H), 2.42 (t, J=6.6 Hz, 2H), 2.04 (s, 3H), 1.85 (m, 1H), 167 (m, 2H), 1.33 (m, 1H), 0.88 (m, 2H).

EXAMPLE 3
α-chloro-N-hydroxy-N-[(trans-2-phenylcyclopropyl)methyl]acetamide

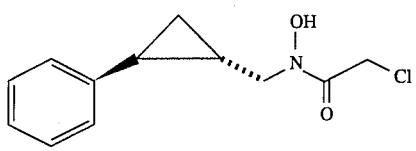

To a stirred solution of N-[(trans-2-phenylcyclopropyl)methyl]-N-hydroxylamine (3.26 g, 20 mM) in methylene chloride (50 ml) was added chloroacetyl chloride (4.52 g, 40 mM) and triethylamine (4.04 g, 40 ml) at room temperature. After stirring for 5 hours, it was poured into saturated aqueous sodium bicarbonate. The whole was extracted with chloroform (2×100 ml). The extracts were washed with water and brine, then were added and evaporated in vacuo. Chromatographic purification (eluent chloroform:ethanol= 15:1) of the residue provided 2 g (41.8% yield) of the desired product as a pale yellow oil.

IR (neat): 3200, 1640, 1500, 1245, 1175, 1090, 1030, 925.

NMR (DMSO-d6): 10.09 (s, 1H), 7.10 (m, 5H), 4.40 (s, 2H), 3.57 (d, J=7.0 Hz, 2H), 1.88 (m, 1H), 1.37 (m, 1H), 0.94 (m, 1H).

EXAMPLE 4
N-hydroxy-N-[(trans-2-phenyl-1-cyclopropyl)methyl]-α-(1-pyrrolidino)acetamide

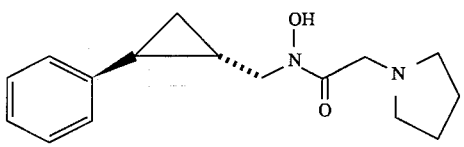

To a stirred solution of α-chloro-N-hydroxy-N-[(trans-2-phenylcyclopropyl)methyl]acetamide (0.75 g, 3.13 mM) in THF (7 ml) was added pyrrolidine (0.29 g, 4.07 mM) at room temperature. After stirring for 2 hours, volatiles were removed in vacuo. Ethyl acetate and saturated aqueous sodium bicarbonate was added to the residue and the whole was extracted with ethyl acetate. The extracts were washed with brine then dried and evaporated in vacuo. The resulting residue was triturated with diethylether and filtered to afford 0.532 g (62% yield) of the desired product as a colorless solid, m.p. 101°–102.5° C.

IR (nujol): 1650, 1260, 1180, 1160, 1020, 880, 755, 700.

NMR (DMSO-d6): 9.79 (s, 1H), 7.18 (m, 4H), 3.52 (d, J=6.6 Hz, 2H), 3.36 (s, 2H), 2.50 (m, 4H), 1.88 (m, 1H), 1.66 (br s, 4H), 1.34 (m, 1H), 0.92 (m, 2H).

We claim:
1. A compound of the formula

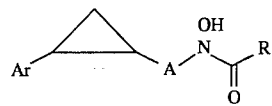

or a pharmaceutically acceptable salt thereof, wherein:
A is C1 to C3 alkylene;
Ar is phenyl;

R is halosubstituted C1 to C3 alkyl, NHR' or

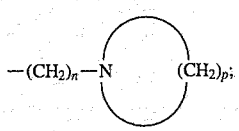

R' is C2 to C8 alkylthioalkyl;
n is an integer of from 1 to 4; and
p is an integer of from 2 to 5.

2. A compound according to claim 1 wherein:
Ar is phenyl; and
R' is C2 to C8 alkylthioalkyl.

3. A compound according to claim 1 wherein:
Ar is phenyl; and
R is halosubstituted C1 to C3 alkyl.

4. A compound according to claim 1 wherein:
Ar is phenyl; and
R is pyrrolidinomethyl.

5. A compound according to claim 1 selected from: N-hydroxy-N'-(3-methylthiopropyl)-N-[(trans-2-phenylcyclopropyl)methyl]urea; α-chloro-N-hydroxy-N-[(trans-2-phenylcyclopropyl)methyl]acetamide; and N-hydroxy-N-[(trans-2-phenyl-1-cyclopropyl)methyl]-α-(1-pyrrolidino)acetamide.

6. A pharmaceutical composition for the treatment of allergy, inflammatory or cardiovascular conditions in a mammal comprising a therapeutically effective amount of a compound according to claim 1 or a pharmaceutically acceptable salt thereof together with a pharmaceutically acceptable carrier.

7. A pharmaceutical composition for the treatment of allergy, inflammatory or cardiovascular conditions in a mammal comprising a therapeutically effective amount of a compound according to claim 5 or a pharmaceutically acceptable salt thereof together with a pharmaceutically acceptable carrier.

8. A method of inhibiting lipoxygenase in a mammal comprising administering to said mammal a lipoxygenase-inhibiting amount of a compound according to claim 1 or a pharmaceutically acceptable salt thereof.

9. A method of inhibiting lipoxygenase in a mammal comprising administering to said mammal a lipoxygenase-inhibiting amount of a compound according to claim 5 or a pharmaceutically acceptable salt thereof.

10. A method of treating allergy or inflammatory or cardiovascular conditions in a mammal comprising administering to said mammal a lipoxygenase-inhibiting amount of a compound according to claim 1 or a pharmaceutically acceptable salt thereof.

11. A method of treating allergy or inflammatory or cardiovascular conditions in a mammal comprising administering to said mammal a lipoxygenase-inhibiting amount of a compound according to claim 5 or a pharmaceutically acceptable salt thereof.

* * * * *